(12) United States Patent
Xu (10) Patent No.: US 12,044,605 B2
(45) Date of Patent: Jul. 23, 2024

(54) PLATELET FUNCTION DETECTION SYSTEM AND DETECTION METHOD

(71) Applicant: SINNOWA MEDICAL SCIENCE & TECHNOLOGY CO., LTD., Nanjing (CN)

(72) Inventor: Xin Xu, Nanjing (CN)

(73) Assignee: SINNOWA MEDICAL SCIENCE & TECHNOLOGY CO., LTD., Nanjing (CN)

( * ) Notice: Subject to any disclaimer, the term of this patent is extended or adjusted under 35 U.S.C. 154(b) by 355 days.

(21) Appl. No.: 17/597,312

(22) PCT Filed: Aug. 5, 2019

(86) PCT No.: PCT/CN2019/099172
§ 371 (c)(1),
(2) Date: Jan. 3, 2022

(87) PCT Pub. No.: WO2021/003786
PCT Pub. Date: Jan. 14, 2021

(65) Prior Publication Data
US 2022/0317011 A1 Oct. 6, 2022

(30) Foreign Application Priority Data
Jul. 10, 2019 (CN) .......................... 201910619683.1

(51) Int. Cl.
*G01N 15/0205* (2024.01)
*A61M 1/36* (2006.01)
(Continued)

(52) U.S. Cl.
CPC ....... *G01N 15/0205* (2013.01); *A61M 1/3693* (2013.01); *G01N 21/31* (2013.01); *G01N 33/5002* (2013.01); *G01N 2015/018* (2024.01)

(58) Field of Classification Search
CPC ............... G01N 15/0205; G01N 21/31; G01N 33/5002; G01N 2015/018; A61M 1/3693
See application file for complete search history.

(56) References Cited

U.S. PATENT DOCUMENTS

2019/0143324 A1\* 5/2019 Wang ................ B01L 3/502707
435/6.12
2020/0171501 A1\* 6/2020 McEwen ........... B01L 3/502792

FOREIGN PATENT DOCUMENTS

CN 204758612 U \* 11/2015

OTHER PUBLICATIONS

Amanda G. M. Perez et al., "Relevant Aspects of Centrifugation Step in the Preparation of Platelet-Rich Plasmas", Mar. 25, 2014, Hindawi Publishing Corporation—ISRN Hematology, vol. 2014, Article ID 176060 (Year: 2014).\*

\* cited by examiner

*Primary Examiner* — Edmond C Lau
*Assistant Examiner* — Joshua M Carlson
(74) *Attorney, Agent, or Firm* — CBM PATENT CONSULTING, LLC (57) ABSTRACT

A system consists of a detector and a detection card (9); the detector comprises a separation-detection turntable (4), a drive motor (3), a detection unit (5), a control and analysis unit (1), and a display unit (2); more than one detection card positions are arranged on the separation-detection turntable (4), and the separation-detection turntable (4) is driven by the drive motor (3) to rotate, so as to mix, separate and detect samples in the detection card; and the detection cards (9) are loaded on the detection card positions on the turntable, the detection card (9) is internally divided into more than two inner cavity pools, the divided inner cavity pools are respectively connected by narrow channels with a cross-sectional area less than 60% of a maximum cross-sectional area of (Continued)

each inner cavity pool, and all the inner cavity pools are unidirectionally connected in series.

10 Claims, 5 Drawing Sheets

(51) Int. Cl.
  *G01N 15/01* (2024.01)
  *G01N 21/31* (2006.01)
  *G01N 33/50* (2006.01)

PLATELET FUNCTION DETECTION SYSTEM AND DETECTION METHOD

TECHNICAL FIELD

The present invention relates to a platelet function detection technology, and more particularly, to a platelet function detection system and detection method.

BACKGROUND

Thrombotic diseases are the most harmful diseases to the human health and life in the world currently. Controlling platelet function is the most common and frequently used way to prevent and treat thrombosis. However, due to individual differences of patients and differences in drug responses, the current method of "standardized" application of anti-platelet drugs to all patients shows obvious problems in clinic, comprising inability of effectively preventing and treating the thrombotic diseases, or occurrence of bleeding hazards to the patients due to excessive administration. Moreover, in recent 10 years, it has been confirmed by studies that the individual differences response to anti-platelet drugs is very widespread. Therefore, it is very important to detect the platelet function in the prevention and treatment of thrombosis, which is an important measure to achieve accurate prevention and treatment of thrombosis and improve prevention and treatment levels of thrombosis.

Although the detection of the platelet function has been implemented for more than 50 years, the existing platelet function detection methods have obvious shortcomings such as poor accuracy, slow speed and inability of detecting on a large scale at a high speed. For example, Light Transmitting Assay (LTA) is the oldest platelet function detection method, which requires repeated centrifugation of sample detection and manual separation of platelet-rich plasma and platelet-poor plasma, with extremely cumbersome operations. Moreover, too many pre-test operation often activate the platelets before detection, which causes the detection results to be inconsistent with the actual situations of the platelet functions in bodies of the patients. In recent years, some instruments for directly detecting the platelet function in whole blood have also appeared on the market, but these instruments often fail to effectively eliminate the interference of red blood cells and other constituents. Since the number of the red blood cells in normal blood samples is far greater than that of platelets, and the volume of the red blood cells is also far greater than that of platelets, if the interference of the red blood cells on a detection signal cannot be eliminated when detecting the platelet function, the signal of direct detection of the platelets is weaker, and accurate detection results of the platelet function cannot be obtained. In recent years, most clinical trials completed by different methods published at home and abroad are ended in failure.

SUMMARY

An objective of the present invention is to provide a platelet function detection system and detection method.

The technical solutions for achieving the objective of the present invention are as follows: a platelet function detection system, wherein the detection system consists of two parts comprising a detector and a detection card;

the detector comprises a separation-detection turntable, a drive motor, a detection unit, a control and analysis unit, and a display unit, the separation-detection turntable is located in an operating room of the detector, and the operating room of the detector has a thermostat function;

more than one detection card positions are arranged on the separation-detection turntable, and the separation-detection turntable is driven by the drive motor to rotate, so as to mix, separate and detect samples in the detection card; the detection unit comprises a light source transmitter and a receiver, and is used for detecting the samples, the control and analysis unit is used for controlling the separation-detection turntable, the drive motor and the detection unit, and generating a platelet function detection result report by calculation and analysis according to a detection signal, and the display unit is used for displaying a detection result and human-computer interaction; and the detection card is arranged on the detection card position, the detection card is internally divided into more than two inner cavity pools, the inner cavity pools are respectively connected by narrow channels with a cross-sectional area less than 60% of a maximum cross-sectional area of each inner cavity pool, and all the inner cavity pools are unidirectionally connected in series; and at least one inner cavity of the detection card is made of a transparent material, and the detection card is capable for optical signal detection on a sample in the inner cavity.

A platelet function detection method comprises the following steps of:

step 1: after adding a sample and an agonist into the reaction pool A of the sample detection card, placing and fixing the sample detection card on the detection card position on the separation-detection turntable of the detector; synchronously adding an equal amount of the same blood sample into a pool A of a control detection card, with a same structure, and adding an equal amount as agonist of isotonic diluent or anticoagulant into the pool A of the control detection card;

step 2: enabling the detector, so that the separation-detection turntable starts to rotate back and forth repeatedly, so that the blood sample and the agonist are mixed and reacted in the pool A of the sample detection card for more than 3 minutes, and maintaining the operating room of the detector at a constant temperature;

step 3: the separation-detection turntable rotating at first speed unidirectionally, so that the samples with agonist in the pools A of the sample detection card and the control detection card move into pools B and pools C under the drive of centrifugal force, and the samples are separated during centrifugation due to different proportions of different components in the blood samples: red blood cells, white blood cells and aggregated platelet complexes enter the pools C; and the plasma and monomer platelets distributed in the plasma enter the pools B;

step 4: the separation-detection turntable of the detector rotating at a low speed, and detecting, by the detection unit of the detector, absorbances of the pools B of the sample detection card and the control detection card one by one for the first time;

step 5: after completing the first time detecting, the separation-detection turntable continuously turning into second speed rotating at a higher speed, so that the original monomer platelets in the plasma in the pools B are deposited into the pools C under the action of a centrifugal force in higher speed centrifugation, and then detecting, by the detector, the pools B of the sample detection card and the control detection card again to obtain blank values of the plasma in the pools B of the detection cards; and step 6: calculating results of platelet aggregation rates of the blood samples of the detection cards:

Net content value of platelets in pool $B$ of control detection card (Cd)=absorbance value obtained by detection of pool $B$ of control detection card for the first time–blank absorbance value of pool $B$ of control detection card; and Net content value of platelets of blood sample in pool $B$ of sample detection card (Sd)=absorbance value obtained by detection of pool $B$ of sample detection card for the first time–blank absorbance value of pool $B$ of sample detection card; and According to the above results, calculating the aggregation rate of the platelets (Ar) with a formula as follows:

$$Ar=(Cd-Sd)/Cd\times 100\%.$$

Compared with the prior arts, the present invention has the obvious advantages as follows: (1) convenient detection is realized: the whole blood is directly used, and the platelets in the sample are detected after the red blood cells and the white blood cells in the blood sample are automatically separated, thus avoiding cell interference; (2) the function of any platelet receptor may be detected, which sufficiently meets clinical needs; (3) rapid detection is realized, which may be not only suitable for bedside detection of a small number of samples, but also suitable for rapid batch detection of a large number of samples; (4) differences caused by the cells of samples and by the detection cards are effectively eliminated through the detection solution, so that the quality of the detection results may be better ensured; (5) the method does not need manual participation, the detector automatically completes the mixing, reacting of the blood sample and the reagent; separating of the plasma, and accurately detects and compares the contents of the platelets in the sample card and the control card, thus obtaining the change of the platelet numbers caused by stimulation and activation of the agonist, and directly reflecting the platelet function, and through the detection method, the quality of the sample may also be effectively monitored, and the error of the detection results caused by the activation and aggregation of the platelet function in the sample before detection may be eliminated; and (6) less reagents are consumed and less wastes are produced.

BRIEF DESCRIPTION OF THE DRAWINGS

FIG. 1 is a composition diagram of a detector. In the figure, 1 refers to a control unit of a detector, 2 refers to a display unit, 3 refers to a drive motor, 4 refers to a separation-detection turntable, 5 refers to a detection unit, 6 refers to a printer, 7 refers to a light source, 8 refers to a detecting receiver, and 9 refers to a detection card fixed on the separation-detection turntable.

DETAILED DESCRIPTION

Platelet functions are multifaceted, which serve as important factors to maintain normal physiology and health of a body, and also play an important role in the pathological process of various diseases. To detect the platelet functions has significant scientific research and clinic values, but there are shortcomings in the existing platelet function detection methods, so that applications of the platelet function detection in scientific research and clinic are limited. Therefore, a simple and rapid platelet function detection method and a detector with small sample consumption and automatic calibration and elimination of detection errors are designed. The detector, in cooperation with a specially designed matching detection card, is capable of automatically completing the whole process of mixing and reacting of sample and reagent, separating and detecting. The detector is further designed with various quality control measures, ensuring precise detection result.

Figure 1:
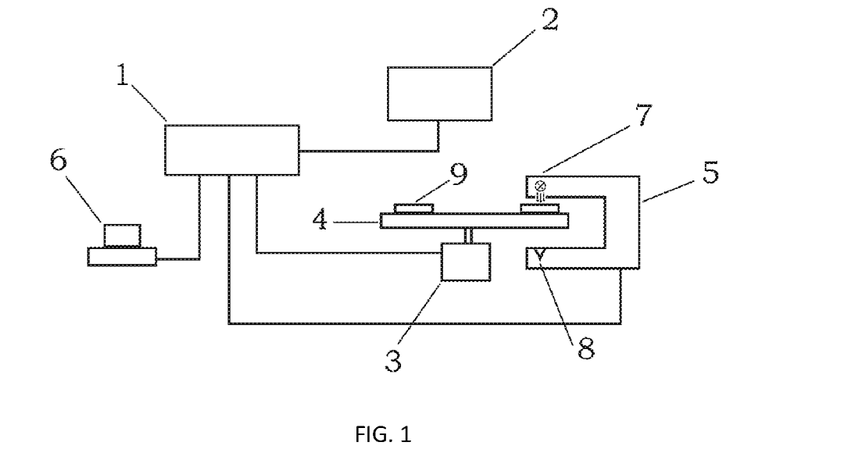

As shown in FIG. 1, a platelet function detection system consists of two parts comprising a detector and detection cards.

The detector comprises a separation-detection turntable 4, a drive motor 3, a detection unit 5, a control and analysis unit 1, and a display unit 2. The separation-detection turntable is located in an operating room of the detector, and the operating room of the detector has a thermostat function.

More than one detection card positions are arranged on the separation-detection turntable, and the separation-detection turntable is driven by the drive motor to rotate and rotate back and forth to mix the sample and reagent, and then separate blood samples in detection cards by rotating and centrifugation, and the separation-detection turntable is driven to rotate to make detection pools of the detection cards and a control card on the turntable pass through the detection unit one by one, and detection results are obtained. The detection unit comprises a light source transmitter 7 and a receiver 8, and is used for detecting the separated samples in the detection cards. The control and analysis unit is used for controlling the separation-detection turntable and the drive motor, recording detection data at the same time, and generating a platelet function detection result report. The display unit is used for displaying a detection result and human-computer interaction, and the detection result is printed by a printer 6. A detector automatically completes all the process of sample-reagent mixing, separating, detecting, analysis and result reporting.

The detection card 9 is arranged on the detection card position, and the detection card is firmly fixed on the separation-detection turntable by using a fixing card device 11 and an adjustable fixing device 10. The detection card is of a closed structure entirely to the tail portion except an inlet opening, or a tail portion of the pool C has a small exhaust channel, which is communicated with an outward opening in the adjacent area of the pool A. The detection card is internally divided into more than two inner cavity pools, the inner cavity pools are respectively connected by narrow channels with a cross-sectional area less than 60% of a maximum cross-sectional area of each inner cavity pool, and all the inner cavity pools are unidirectionally communicated in series. At least one inner cavity of the detection card is made of a transparent material, and the detection card is capable of performing optical signal detection on a sample in the inner cavity.

Further, the separation-detection turntable 4 is arranged in the operating room of the detector, and the operating room of the detector has heating and thermostat functions. The temperature is controlled within a range of 28° C. to 38° C., and reaction and mixing of the sample and the reagent, centrifugation and separation and detection are all completed in the operating room of the detector.

Further, when the detection cards are placed horizontally, a bottom edge of the narrow channel between the inner cavity pools of the detection card is higher than a top portion of an adjacent inner cavity pools.

Further, an angular rotor or a horizontal rotor is employed for the detection card 9.

The separation-detection turntable of the detector may be of a horizontal plate structure, and the detection card is horizontally placed and fixed on the horizontal separation-detection turntable when executing detection, and the detection card is also horizontally placed and fixed.

Further, the detection card is placed and fixed on an angled separation-detection turntable at an angle of 5 degrees to 45 degrees, and is tightly attached to a surface of the detection turntable and fixed on the detection turntable.

An axis of a detection light source of the detection unit is perpendicular to the detection card. The receiver is arranged on a position perpendicular to the detection card and corresponding to the light source, and is used for detecting transmitted light; or the receiver forms a certain angle with detection light, and is used for detecting scattered light.

Figure 3A:
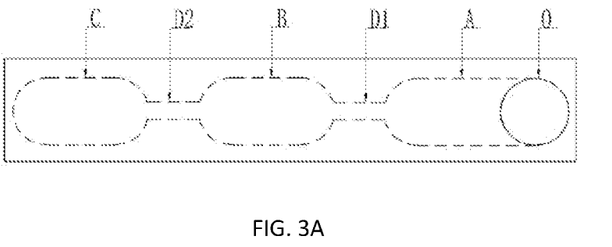
FIG. 3A is a top view of a detection card with three inner cavity pools. In the figure, A refers to a reaction pool, which is connected with an inlet 0, B refers to a detection pool, C refers to a sedimentation pool, and D1 and D2 refer to narrow connecting channels connecting the pool A, the pool B and the pool C respectively.

Further, three inner cavity pools connected in series are arranged inside the detection card, which are a pool A, a pool B and a pool C in sequence. The pool A is a reaction pool, the pool B is a detection pool and the pool C is a sedimentation pool. The pool A is provided with an upward opening perpendicular to an axial direction of the detection card for adding the sample and the reagent, and the sample and the reagent are mixed and reacted in the pool. The pool B is connected with the pool A and the pool C through the narrow channels respectively, the cross-sectional area of the narrow channel is less than 60% of the maximum cross-sectional area of each inner cavity pool, and in addition to this, the pool B has no other opening. A tail portion of the pool C has a small exhaust channel, which is communicated with an outward opening in the adjacent area of the pool A. However, the channel is not communicated with the pool A, and is used for exhausting original air in the pool B and the pool C during centrifugal separation of the sample, thus being convenient for allowing the sample to enter the pool B and the pool C, and separating components of the sample.

A volume of the pool A is greater than or equal to total volumes of the pool B and the pool C together, the volumes of the pool B and the pool C are similar, and a difference between the volumes of the pool B and the pool C is no more than 30%. Connecting channels between the pools are the narrow channels with the cross-sectional area less than 60% of the maximum cross-sectional area of each pool.

In another embodiment, two inner cavity pools distinguished and communicated by the narrow channel are arranged in the detection card, one inner cavity pool is used as both a reaction pool and a detection pool, and the other inner cavity pool without an outward opening serves as a sedimentation pool.

The present invention further provides a detection method based on the platelet function detection system, which comprises the following steps.

In step 1, after adding a sample and an agonist into the reaction pool A of the detection card respectively, the detection card is placed and fixed on the detection card position on the separation-detection turntable of the detector. An equal amount of the same blood sample is synchronously added into a pool A of a control detection card with a same structure, and an equal amount as agonist of isotonic diluent or anticoagulant is added into the pool A of the control detection card. Since the difference may be ignored when a small amount of reagent is added during detection, the equal amount of isotonic diluent or anticoagulant may not be added into the pool A of the control card. The control detection card is also fixed on the detection card position on the separation-detection turntable according to a placing mode of the sample detection card.

In step 2, the detector is enabled, the separation-detection turntable starts to rotate back and forth repeatedly for mixing, the blood sample and the agonist in the pool A of the detection card are mixed and reacted for more than 3 minutes, and the operating room of the detector is maintained at a constant temperature ranging from 28° C. to 38° C.

In step 3, after the blood sample and the reagent are mixed evenly, the separation-detection turntable is rotated at a first speed unidirectionally, so that the samples in the pools A of the detection card and the control card flow into pools B and pools C under the drive of a centrifugal force, and the samples are separated during centrifugation due to different proportions of different components in the blood samples: red blood cells, white blood cells and larger aggregated platelet complexes with a large specific gravity entering the pools C; and the plasma and monomer platelets or small platelet complexes with low-degree aggregation distributed in the plasma in the pools B. The centrifugation is performed at 1,000 rpm to 4,000 rpm for 3 minutes to 10 minutes.

In step 4, a rotating speed of the separation-detection turntable of the detector is then reduced, and absorbances of all the pools B of the detection cards are detected by the detection unit of the detector one by one for the first time. At the moment, the detected absorbances (turbidness degrees) are related to the content of the platelets in the plasma. A multi-wavelength may be employed in detection by the detector, or a dye, a marker and the like may be added into the samples to improve specific cell recognition sensitivity. After completing separation, the rotating speed of the separation-detection turntable is lower than 1,000 rpm during the detecting.

In step 5, after completing the detection for the first time, the separation-detection turntable is continuously rotated at a higher speed, the second speed. At the moment, since the rotating speed is higher, the originally suspending monomer platelets in the pools B are deposited into the pools C under the action of a centrifugal force in higher speed centrifugation. The centrifugation is performed at above 4,500 rpm for more than 5 minutes. Then, the pools B of the detection cards and the control detection card are detected by the detector again to obtain blank values of the pools B of the detection cards and the control card.

In step 6, results of contents and aggregation rates of the platelets in the blood samples of the detection cards are calculated.

There is a correlation between the content of the platelets in the plasma and the detected absorbance (O.D. value) after separation of the blood samples. The detector calculates the more accurate content of the platelets in each sample by subtracting the blank value of the pool B from the O.D value obtained by detection of the pool B for the first time. A calculation method is as follows.

Net content value of platelets in pool $B$ of control detection card (Cd)=absorbance value obtained by detection of pool $B$ of control detection card for the first time–blank absorbance value of pool $B$ of control detection card; and Net content value of platelets of blood sample in pool $B$ of sample detection card (Sd)=absorbance value obtained by detection of pool $B$ of sample detection card for the first time–blank absorbance value of pool $B$ of sample detection card; and According to the above results, calculating the aggregation rate of the platelets (Ar) with a formula as follows:

$$Ar=(Cd-Sd)/Cd\times100\%.$$

The rotating speeds of the separation-detection turntable during the two detecting are both reduced. The detector may also dynamically monitor a change of the absorbance in the pool B during centrifugation at first speed. When a separation condition of the sample in the pool B in centrifugation meets the detection, the detector automatically detects and records the absorbance values of the pools B of the detection cards, as the detection of the first time, and then the separation-detection turntable rotates at the second speed to start higher speed separation.

The detection cards and the control card of the same blood sample have the same structure and fixation, and the same separation and detection conditions are employed.

When it is detected that the net content of the platelets in the pool B of the control detection card is too low, which is lower than a content of normal plasma, or lower than a content of the plasma of the sample, the detector will automatically prompt a quality problem of the sample or a condition that the platelets in the sample have highly aggregated before the detecting, and a reliability of detection results of the platelet function obtained under this condition is lower. Therefore, detection errors caused by the sample quality may be avoided.

The specific principle is as follows: an original concentration of the blood sample, which is represented by the concentration of the platelets in the sample not being added with the agonist, is obtained by detecting the control card according to the method and the detector, so as to judge whether the content of the platelets in the control card is lower than a normal concentration range, or if it is lower than an actual concentration range of the platelets of the sample (which may also be judged by referring to a report of a blood analyzer). If the number of the platelets in the control card (which is namely the original blood sample) is lower than a normal range, or is lower than the real range of the sample, the detector automatically prompts that the sample is likely to have been aggregated before detecting, which leads to excessive reduction of the number of the platelets. The authenticity and the credibility of the detection results of the platelet function obtained by detection under the sample condition are lower. Since the platelet function is very easily changed during the sample collection or storage, this function of the detector and the method in the present invention may eliminate false results generated by activation and aggregation of the platelet function before detection, thus avoiding a false report caused by the sample quality.

The detector obtains the concentration (content) of the platelets in the blood sample by detecting the pool B of the control detection card, and specific detection and result calculation methods are as follows: (absorbance value obtained by detecting pool B of control detection card after centrifugation for the first time–absorbance value obtained by detecting pool B of the control detection card after centrifugation for the second time)*K value. The K value is a correlation coefficient between the content of the platelets and the net absorbance value of the platelets in the plasma, and the K value ranges from 100 to 3,000, in a unit of 10,000/ml, which may also be converted into other units. The K value of each detector needs to be calibrated and confirmed.

The detector has a function of automatically analyzing separation of the blood sample online. Multiple wavelengths (ranging from 260 nm to 700 nm) are employed in the detector to analyze sedimentation and content conditions of cell components such as red blood cells, white blood cells and platelets in the sample. When the RBCs and the WBCs in detection areas are sufficiently settled and separated, the detector starts to perform turbidimetric scanning on contents of the platelets in the detection areas of the cards of the same set of samples, which means that for the samples separated early, the results may be obtained early, and for the samples separated late, the separation time is prolonged to ensure detection after completing separation.

An acridine dye may be added into the blood sample to determine whether the detector separates the WBCs/RBCs from the PLT. Since the WBCs are rich in DNAs capable of being stained, "acridine staining" in the separated plasma of the pool B prompts the existence of the WRCs. For the existence of the RBCs, and a specific absorption wavelength of hemoglobin may also be used for detection. When the RBCs are excessively absorbed in detection, it is indicated that the RBCs are not well separated. These measures may better ensure the accuracy of the detection results of the platelet function.

The detector has functions of determining upper and lower interface heights of a supernatant after sample separation in the detection card and scanning the whole process.

A plurality of different wavelengths is employed in the detector. Since a particle size causes differences in transmission and scattering of different wavelengths, the detector has a function of analyzing a proportion of particles of different sizes in a turbidity of the supernatant after separation of the sample in the detection card by using absorbance differences of different wavelengths.

The present invention is described in detail hereinafter with reference to the accompanying drawings and the embodiments.

Embodiment 1

As shown in FIG. 1, a platelet function detection system consists of two parts comprising a detector and a detection card. The detector comprises a separation-detection turntable 4, a drive motor 3, a detection unit 5, a control and analysis unit 1, and a display unit 2. More than one detection card positions are arranged on the separation-detection turntable for placing a detection card and a control card. The detection card and the control card have the same structure, are only different in a condition whether a reagent is added in detection (agonist is not added for the control card), and play different roles in detection. The separation-detection turntable is driven by the drive motor to rotate back and forth firstly, so as to evenly mix samples and reagent in pools A of the cards and then the separation-detection turntable centrifugally rotates at a first speed to separate the samples in the detection cards. The detection unit 5 comprises a light source transmitter 7 and a receiver 8, and is used for detecting the samples. The control and analysis unit 1 is used for controlling the separation-detection turntable and the drive motor, and generating a platelet function detection result report by analyzing and processing detection data at the same time, and the detection results are printed by a printer 6. The detector automatically completes all the process of mixing, separation, detection, analysis and result report.

Figure 2A:
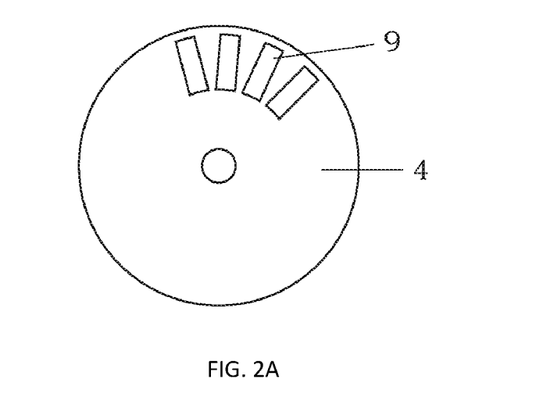
FIG. 2A is a top view of the separation-detection turntable of the detector with a horizontal plate structure.
Figure 2B:
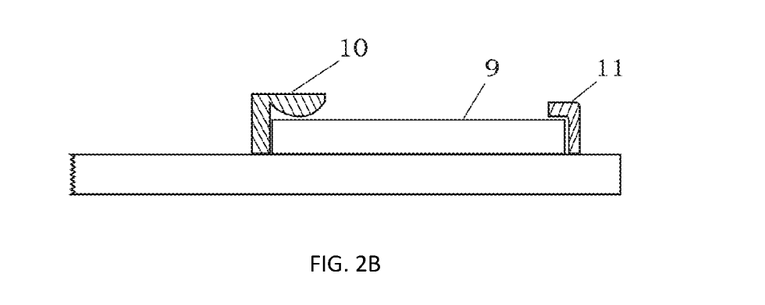
FIG. 2B is a schematic diagram showing positions of the separation-detection turntable of the detector and a detection card. In the figure, 10 refers to an adjustable fixing device of the detection card, and 11 refers to a device for fixing the detection card.

As shown in FIG. 2A and FIG. 2B, the separation-detection turntable is of a horizontal plate structure, and the detection card 9 is fixed on the separation-detection turntable through a fixing device 11 and an adjustable fixing device 10 of the detection card.

The detection card 9 and the control card are arranged on the detection card positions, and the detection card 9 is internally provided with three cavity pools, comprising a pool A of a reaction pool, a pool B of a detection pool and a pool C of a sedimentation pool in sequence. The inner cavity pools are respectively connected by narrow channels with a cross-sectional area less than 60% of a maximum cross-sectional area of each inner cavity pool, and all the inner cavity pools are unidirectionally communicated in series.

Figure 3B:
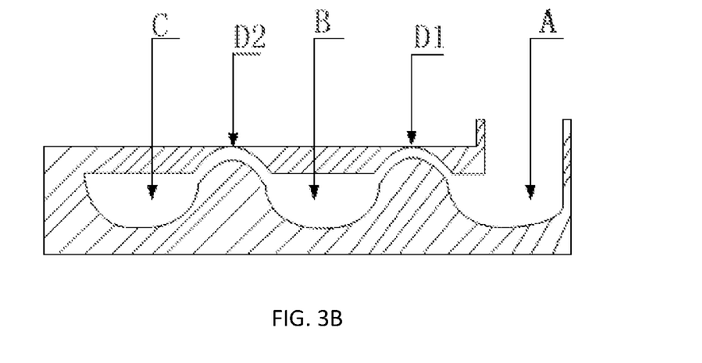
FIG. 3B is a longitudinal sectional view of the detection card with three inner cavity pools.

A detection card is shown in FIG. 3A, wherein A, B and C are three inner cavities respectively, D1 and D2 are narrow channels connecting the three inner cavities respectively, and O is an opening of the detection card, which is located in the pool A. As shown in FIG. 3B, the inner cavity pool A is provided with an opening perpendicular to an axial direction of the detection card. Moreover, bottom edges of the narrow channels D1 and D2 connecting the pool A, the pool B and the pool C (inner cavities) are both higher than top portions of the inner cavity pool B and the inner cavity pool C. This design may avoid the samples from refluxing after completing centrifugation.

By using the detector above, a platelet function detection method is as follows.

Figure 4:
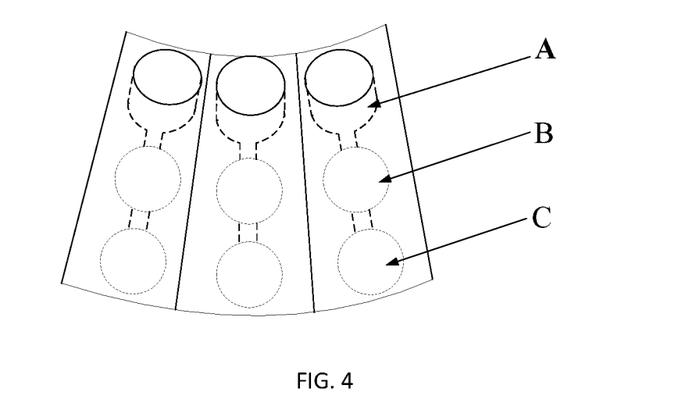
FIG. 4 is a top view of a triple detection card structure composed of three single detection cards.

1. Samples and reagents are respectively added into the pools A of the detection cards, as shown in FIG. 4, wherein one detection card is only added with samples and not added with reagents as control, or the same amount of isotonic saline or anticoagulant as the reagent is also added into the pool A of the control card.
2. The detector is enabled, and the turntable loaded with the sample cards rotates left and right for a plurality of times to evenly mix the reagents and the blood samples in the pools A.
3. The turntable of the detector is centrifuged at a medium speed, first speed, so that the blood samples flow from the pools A into the corresponding pools B and pools C respectively, white blood cells, red blood cells and aggregated platelet aggregates are centrifuged into the pools C, and the non-aggregated platelets and the plasma are concentrated in the pools B.
4. The detector detects absorbances of the pools B to judge concentrations/contents of the remaining platelets in the plasma after the blood samples react with the agonist, and detect the control pool to judge concentrations/contents of the platelets of the blood samples.
5. If it is found through detection that the RBCs or the WBCs still exist in some sample pools B, the detector continues to centrifuge again and detects the pools B which are not well centrifuged again. The pools B of the same blood samples are compared with each other detection card with the same sample. This detection is classified as the detection for the first time.
6. After completing the detection of the first time, the separation-detection turntable of the detector rotates and centrifuges at a higher speed, so that the platelets in the pools B are also centrifugally deposited into the pools C or the channels between the pools B and the pools C.
7. The detector detects the pools B again, and this detection is the detection for the second time, and blank values of the pools B are obtained.
8. The detector calculates and reports aggregation functions of the blood samples under the actions of different agonists.

Embodiment 2

Figure 3C:
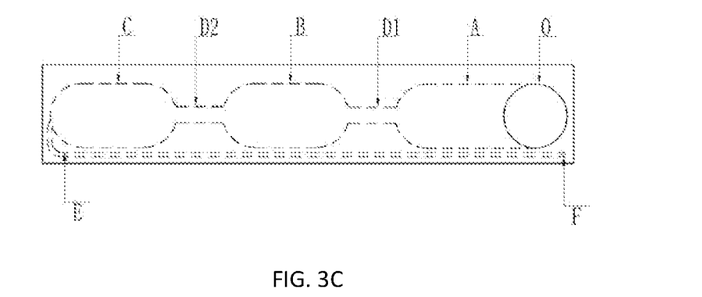
FIG. 3C is a top perspective view of a detection card with three inner cavity pools; different from FIG. 3A, the card has a tiny exhaust channel E leading from the pool C to a vicinity of the pool A of the detection card and provided with an opening F communicated with the outside.

As shown in FIG. 3C, this embodiment is different from Embodiment 1 in that the final inner cavity pool C of the detection card is provided with a tiny exhaust channel E, which is provided with an opening F leading to a vicinity of an inlet for exhausting gas/air pressure in an inner cavity at a tail end.

Embodiment 3

As shown in FIG. 4, in this embodiment, the detection card is a combined detection card composed of three identical monomer detection cards arranged in a fan shape. Each independent card in the combined card contains the same inner cavity and channel, and the independent cards of the combined card are not communicated with each other. An inlet of each independent card is an angular opening perpendicular to an axial direction of the card, and the opening is upward. The combined detection card may be a complex structure composed of 2 to 10 independent detection cards which have the same structure but without any channel connected with each other inside the cards.

Embodiment 4

Figure 5A:
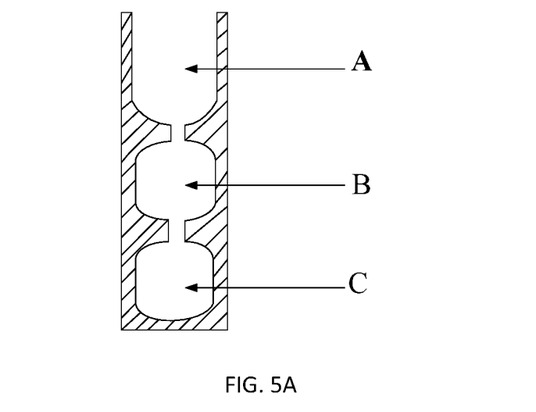
FIG. 5A is a longitudinal sectional view of a detection card with an opening at a top end.
Figure 5B:
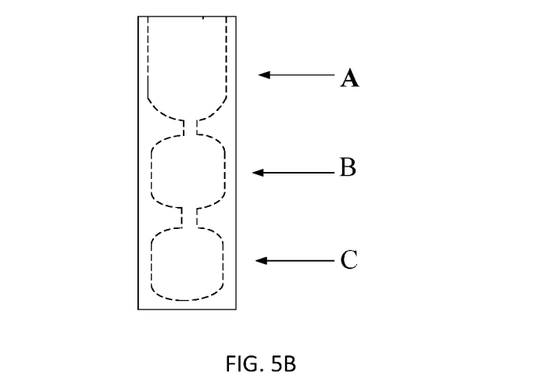
FIG. 5B is a side perspective view of FIG. 5A.

As shown in FIG. 5A and FIG. 5B, this embodiment provides a detection card with an opening at a top end, the card is internally provided with three inner cavities, and the opening is arranged at the top end of the detection card in a direction consistent with an axial direction of the detection card. The detection card with the opening at the top end may be combined to form a complex multi-combination detection card composed of 2 to 8 independent cards, and a structure of the complex multi-combination detection card is matched with the separation-detection turntable, which is convenient for fixing and detection.

Embodiment 5

Figure 6A:
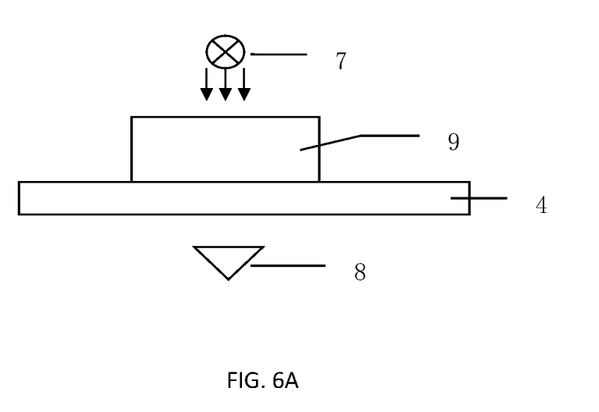
FIG. 6A is a schematic diagram of the combination of a horizontal separation-detection turntable executing transmitted light detection and detection card.

As shown in FIG. 6A, on the horizontal separation-detection turntable, the light source 7 and the detector 8 are arranged in corresponding positions, and the detector may execute transmitted light detection on the detection card.

Embodiment 6

Figure 6B:
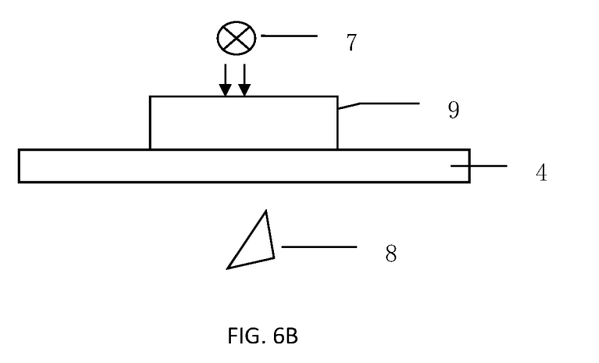
FIG. 6B is a schematic structural diagram of a horizontal separation-detection turntable executing scattering detection.

As shown in FIG. 6B, on the horizontal separation-detection turntable, the light source vertically irradiates the detection card, and an included angle of 20 degrees to 45 degrees is formed between light signal detection and an irradiation direction of the light source. The detector may execute scattering detection on the detection card.

Embodiment 7

Figure 6C:
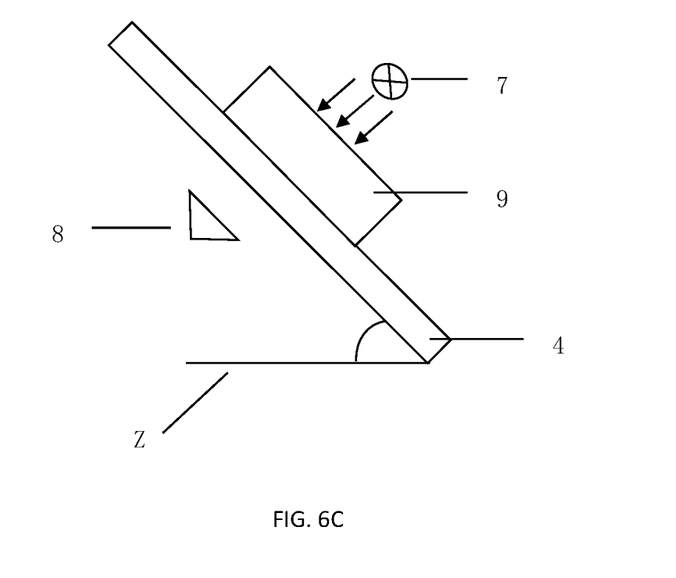
FIG. 6C is a schematic diagram of an angular separation-detection turntable executing transmission detection.

As shown in FIG. 6C, an included angle of 5 degrees to 45 degrees is formed between the separation-detection turntable 4 and a horizontal plane Z. The detection light source 7 is perpendicular to the detection card 9 on the device, and the detector 8 is also perpendicular to the detection card 9 and is arranged in accurate correspondence with the light source. The device may execute transmission detection.

Embodiment 8

Figure 6D:
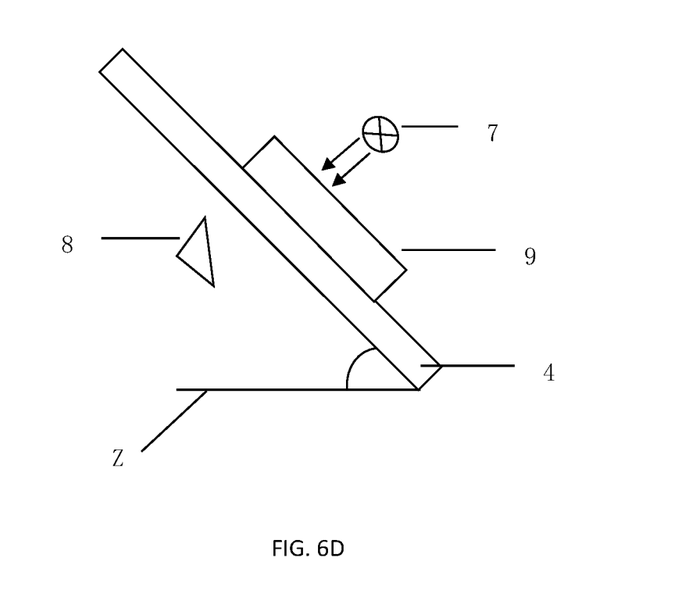
FIG. 6D is a schematic diagram of an angular separation-detection turntable executing scattering detection.

As shown in FIG. 6D, an included angle of 5 degrees to 45 degrees is formed between the separation-detection turntable 4 and the horizontal plane Z. The detection light source 7 vertically irradiates the detection card on the device, the light detector 8 is arranged on a position corresponding to the light source, and a receiving plane is correspondingly arranged to form an included angle of 15 degrees to 45 degrees with the detection card. The device may execute scattering detection.

What is claimed is:

1. A method for detecting platelet function by a platelet function detection system, comprising the following steps of:
   step 1: after adding a blood sample and an agonist into a reaction pool A of a sample detection card, placing and fixing the sample detection card on a detection card position on a separation-detection turntable of a detector; synchronously and equally adding an equal amount of the blood sample into a pool A of a control detection card, with a same structure, and adding an equal amount as agonist of isotonic diluent or anticoagulant into the pool A of a control detection card;
   step 2: enabling the detector, so that the separation-detection turntable starts to rotate back and forth repeatedly, so that the blood sample and the agonist are mixed and reacted in the pool A of the sample detection card for more than 3 minutes, and maintaining an operating room of the detector at a constant temperature;
   step 3: the separation-detection turntable rotating at first speed unidirectionally, so that samples with agonist in the pool A of the sample detection card and the control detection card move into pool B and pool C under a drive of centrifugal force, and the samples with agonist are separated during centrifugation due to different proportions of different components in the blood sample: red blood cells, white blood cells and aggregated platelet complexes enter the pool C; and plasma and monomer platelets distributed enter the pool B;
   step 4: the separation-detection turntable of the detector rotating at a low speed, and detecting, by a detection unit of the detector, absorbances of the pool B of the sample detection card and the control detection card one by one;
   step 5: the separation-detection turntable continuously turning into second speed rotating at a higher speed, so that the monomer platelets in the pool B are deposited into the pool C under the drive of centrifugal force in higher speed centrifugation, and then detecting, by the detector, the pool B of the sample detection card and the control detection card again to obtain blank values of the plasma in the pool B of all the detection cards; and
   step 6: calculating results of aggregation rates of platelets in the blood sample of the detection cards:

a net content value of platelets in the pool $B$ of control detection card (Cd)=absorbance value obtained by detection of the pool $B$ of control detection card for first time–blank absorbance value of the pool $B$ of control detection card; and the net content value of platelets in the blood sample in the pool $B$ of sample detection card (Sd)=absorbance value obtained by detection of the pool $B$ of sample detection card for the first time–blank absorbance value of the pool $B$ of sample detection card; and according to the above results, calculating an aggregation rate of the platelets (Ar) with a formula as follows:

$Ar=(Cd-Sd)/Cd\times 100\%$.

2. The platelet function detection method according to claim 1, wherein according to the method, whether the net content value of platelets in the pool B of the control detection card is lower than a normal concentration range, or lower than a concentration range of the platelets in the blood sample is judged by detecting the control detection card to obtain the net content value of platelets in the blood sample, and if the net content value of platelets in the blood sample the sample detection card is lower than the normal concentration range, or lower than the concentration range of the platelets in the blood sample, the detector automatically prompts that the sample is already aggregated before detection, which leads to decrease of platelet counts; and
   the detector obtains the net content value of platelets in the blood sample by detecting the pool B of the control detection card, and specific detection and result calculation methods are as follows: (absorbance value obtained by detecting the pool B of the control detection card after a first centrifugation–absorbance value obtained by detecting the pool Bs of the control detection card after a second centrifugation)*K value, wherein the K value is a correlation coefficient between the net content value of the platelets in the pool B of the control detection card and a net absorbance value of the platelets in the pool B, and the K value ranges from 100 to 3,000×10,000/ml.

3. The method according to claim 1, wherein the platelet function detection system comprises a detector and a detection card;
   the detector comprises a separation-detection turntable, a drive motor, a detection unit, a control and analysis unit, and a display unit, the separation-detection turntable is located in an operating room of the detector, and the operating room of the detector has a thermostat function;

more than one detection card positions are arranged on the separation-detection turntable, and the separation-detection turntable is driven by the drive motor to rotate, so as to mix, separate and detect samples in the detection card; the detection unit comprises a light source transmitter and a receiver, and is used for detecting the samples, the control and analysis unit is used for controlling the separation-detection turntable, the drive motor and the detection unit, and generating a platelet function detection result report by calculation and analysis according to a detection signal, and the display unit is used for displaying a detection result and human-computer interaction; and the detection card is arranged on the detection card position, the detection card is internally divided into more than two inner cavity pools, the inner cavity pools are connected by narrow channels with a cross-sectional area less than 60% of a maximum cross-sectional area of each inner cavity pool, and all the inner cavity pools are unidirectionally connected; and at least one inner cavity of the detection card is made of a transparent material, and the detection card enables optical signal detection of a sample in the inner cavity.

4. The method according to claim 3, wherein when the detection cards are placed horizontally, a bottom edge of the narrow channel between the inner cavity pools of the detection card is higher than a top portion of an adjacent inner cavity pool.

5. The method according to claim 4, wherein three inner cavity pools connected in series are arranged inside the detection card, which are a pool A, a pool B and a pool C in sequence, the pool A is a reaction pool, the pool B is a detection pool and the pool C is a sedimentation pool; the pool A is provided with an upward opening perpendicular to an axial direction of the detection card for adding a sample and a reagent, and the sample and the reagent are mixed and reacted in the pool A; the pool B is connected with the pool A and the pool C through the narrow channels, the cross-sectional areas of the narrow channels are less than 60% of the maximum cross-sectional area of each inner cavity pool, and except for the connection, the pool B has no direct outward opening; and the pool C is connected with a small exhaust channel, and the small exhaust channel is connected with an outward opening in an area of the pool A for exhausting original air in the pool B and the pool C during centrifugal separation.

6. The method according to claim 5, wherein a volume of the pool A is bigger than or equal to a total volume of the pool B and the pool C together, and a volume difference between the pool B and the pool C is no more than 30%.

7. The method according to claim 4, wherein two inner cavity pools, connected with each other by a narrow channel are arranged inside the detection card, one inner cavity pool is used as both a reaction pool and a detection pool, and another inner cavity pool serves as a sedimentation pool.

8. The method according to claim 3, wherein the detection cards are loaded on an angular rotor or a horizontal rotor.

9. The method according to claim 3, wherein the detection cards are placed and fixed on the separation-detection turntable at an angle of 0 degrees to 45 degrees with a horizontal plane.

10. The method according to claim 3, wherein the separation-detection turntable is arranged inside the operating room of the detector, and the operating room of the detector has heating and thermostat functions; and an axis of a detection light source of the detection unit is perpendicular to the detection card; the receiver is arranged at a position corresponding to the light source and also perpendicular to the detection card, and used for detecting transmitted light; or the receiver is placed at a certain angle with detection light and used for detecting scattered light.

* * * * *